United States Patent
Schnell et al.

(10) Patent No.: US 6,177,049 B1
(45) Date of Patent: Jan. 23, 2001

(54) REVERSING FLOW BLOOD PROCESSING SYSTEM

(75) Inventors: William J. Schnell, Libertyville, IL (US); David S. Utterberg, Seattle, WA (US); Ting Ting Yu, Grayslake, IL (US)

(73) Assignee: DSU Medical Corporation, Las Vegas, NV (US)

( * ) Notice: Under 35 U.S.C. 154(b), the term of this patent shall be extended for 0 days.

(21) Appl. No.: 09/095,873

(22) Filed: Jun. 10, 1998

(51) Int. Cl.[7] .................... A61M 1/14; A61M 37/00; A61M 1/00
(52) U.S. Cl. .................... 422/44; 604/4.01; 604/5.01; 604/28; 604/32; 604/6.1
(58) Field of Search ........................ 604/4, 523, 27, 604/28, 30, 32, 40, 43, 153, 905, 4.01, 5.01, 6.1; 422/44, 48; 210/22, 321, 456, 425; 606/192, 194

(56) References Cited

U.S. PATENT DOCUMENTS

| | | | |
|---|---|---|---|
| 4,086,924 | * | 5/1978 | Latham, Jr. . |
| 4,324,662 | * | 4/1982 | Schnell .................................. 210/646 |
| 4,439,984 | * | 4/1984 | Martin .................................... 60/454 |
| 4,662,871 | * | 5/1987 | Rafelson ............................... 604/119 |
| 4,885,087 | * | 12/1989 | Kopf ................................. 210/321.72 |
| 5,106,363 | * | 4/1992 | Nobuyoshi ............................... 604/4 |
| 5,292,308 | * | 3/1994 | Ryan ...................................... 604/86 |
| 5,336,165 | * | 8/1994 | Twardowski ............................. 604/5 |

(List continued on next page.)

OTHER PUBLICATIONS

Depner and Krivitski "Clinical Measurement of Blood Flow in Hemodialysis Access Fistulae and Grafts by Ultrasound Dilution", ASAIO Journal, Jul.–Sep., 1995, pp. M745–M749.

Mishkin et al. "Specificity and Sensitivity of Ultrasound Dilution for Access Recirculation (AR) Measurements", Journal of the American Society of Nephrology, vol. 7, No. 9, Sep., 1996, one page.

Krivitski "Theory and validation of access flow measurement by dilution technique during hemodialysis", Kidney International, vol. 48, (1995), pp. 244–250.

Kirvitski, N.M. "Novel Method to Measure Access Flow During Hemodialysis by Ultrasound Dilution Technique" ASAIO Journal, vol. 41, p. M741–M745, 1995.

(List continued on next page.)

*Primary Examiner*—Glenn K. Dawson
*Assistant Examiner*—Patricia Bianco
(74) *Attorney, Agent, or Firm*—Garrettson Ellis Seyfarth, Shaw

(57) ABSTRACT

A tubular set is provided for the extracorporeal treatment of blood, for example hemodialysis. The set comprises a patient arterial line and a patient venous line, each line having a patient connector at one end thereof. Each patient line connects at its other end to a reversing flow valve. The valve also connects to respective first ends of a blood processing unit arterial line and a blood processing unit venous line. Each of the unit lines carry a connector at ends opposed to the first ends for connection respectively to arterial and venous ports of a blood processing device, typically a dialyzer. The reversing flow valve has a first position that respectively connects the patient and unit arterial lines with the patient and unit venous lines. The reversing flow valve has a second position that connects the patient arterial line with the unit venous line, and the unit arterial line with the patient venous line. Thus, blood flow between the two patient lines can be reversed without reversing flow through the two unit lines and the connected dialyzer. This permits the easy performance of dialysis access site patency tests, or may be used to avoid blood flow blockage in an implanted catheter.

20 Claims, 3 Drawing Sheets

U.S. PATENT DOCUMENTS

| | | | | |
|---|---|---|---|---|
| 5,395,348 | * | 3/1995 | Ryan | 604/247 |
| 5,453,576 | | 9/1995 | Krivitski . | |
| 5,454,374 | | 10/1995 | Omachi . | |
| 5,492,090 | * | 2/1996 | Bucker | 119/14.01 |
| 5,540,668 | * | 7/1996 | Wilson, Jr. et al. | 604/248 |
| 5,570,026 | | 10/1996 | Buffaloe, IV et al. . | |
| 5,595,182 | | 1/1997 | Krivitski . | |
| 5,605,630 | * | 2/1997 | Shibata | 210/646 |
| 5,631,552 | | 5/1997 | Ogawa et al. . | |
| 5,643,190 | * | 7/1997 | Utterberg | 604/4 |
| 5,644,240 | | 7/1997 | Brugger . | |
| 5,685,989 | | 11/1997 | Krivitski et al. . | |
| 5,807,258 | | 9/1998 | Cimochowski et al. . | |
| 5,817,043 | * | 10/1998 | Utterberg | 604/4 |
| 5,830,365 | | 11/1998 | Schneditz . | |

OTHER PUBLICATIONS

Krivistki, N.M. et al. "Accuracy of Dilution Techniques for Access Flow Measurement During Hemodialysis", American Journal of Kidney Diseases, vol. 31, No. 3, pp. 502–508, 1998.

Krivistki, N.M. et al. "Devleopment of a Method for Measuring Hemodialysis Access Flow: From Idea to Robust Technology", Seminars in Dialysis, vol. 11, No. 2, p. 124–130, 1998.

* cited by examiner

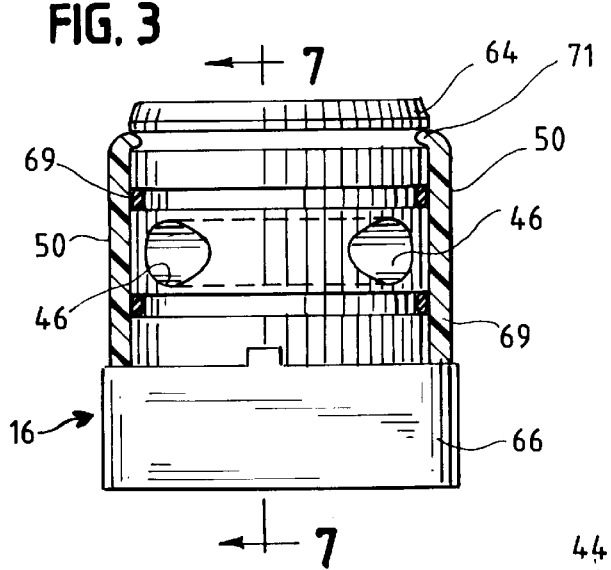
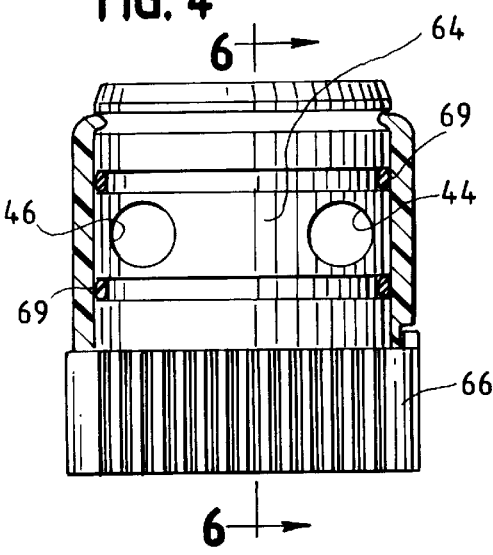
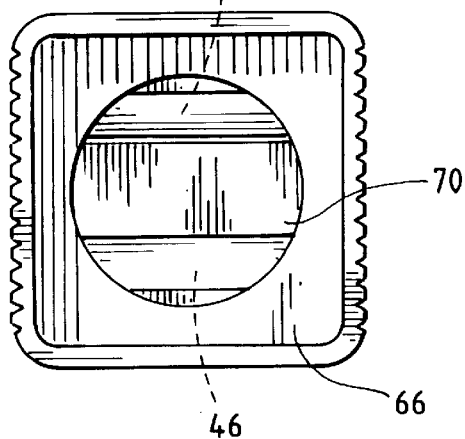
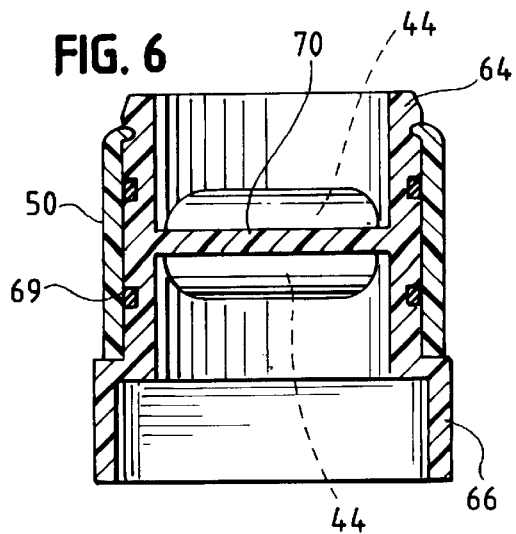
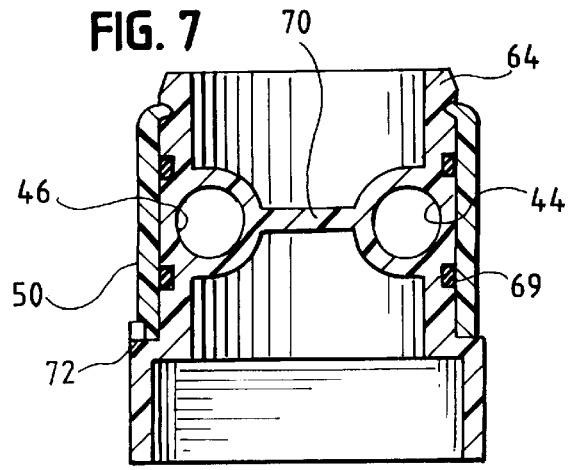

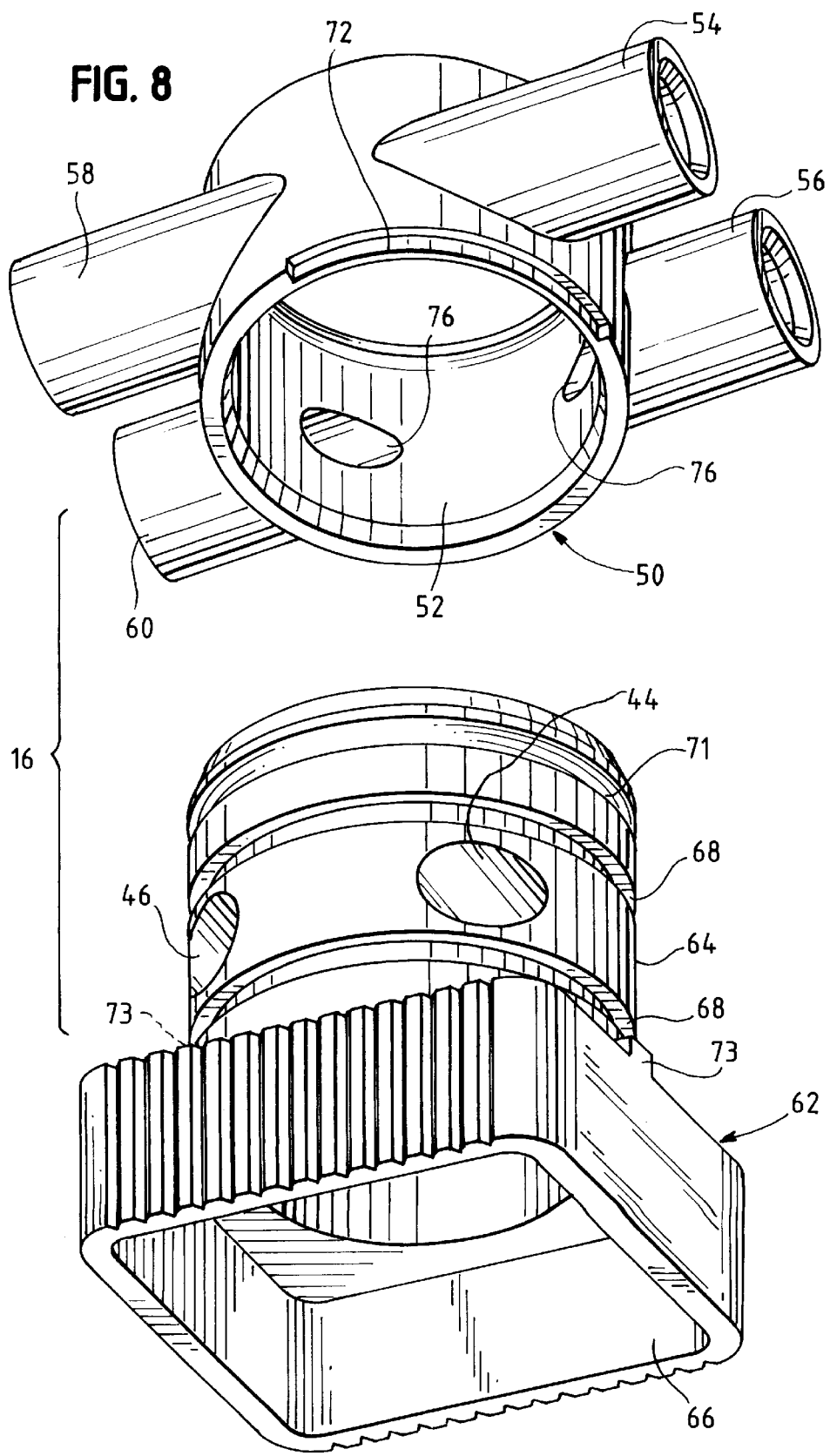

REVERSING FLOW BLOOD PROCESSING SYSTEM

BACKGROUND OF THE INVENTION

Hemodialysis and other forms of extracorporeal blood treatment require the removal of blood from a patient by means of an arterial set, passing of the blood to a blood processing device such as a dialyzer, and returning of the blood to the patient again through a venous blood set.

Maintenance of a good blood set access is a major cost of dialysis, which is the most common extracorporeal blood treatment, although other types of blood treatment are also used, for example passing of the blood through an absorption bed for removal of toxins and the like, hemoperfusion, and other forms of blood treatment.

Beyond the initial cost of the surgical procedure to establish a fistula or graft in the patient, the keeping of adequate blood flow in a modified peripheral blood vessel of the patient frequently involves secondary surgical intervention for reconstruction of an old blood vessel site on the patient. Alternatively, it may be necessary to establish an entirely new fistula or graft at a new site if the old one fails.

Failure is evidenced typically by stenosis of the blood vessel, or blockage of an implanted catheter or other venous access site, with a consequent reduction in blood flow that eventually shuts down the site.

If site failure is detected early enough, a less invasive technique such as balloon angioplasty can be employed to open the stenosis at a greatly reduced cost. Early detection of stenosis can be measured by rise in pressure in the blood vessel or implant that reflects a restriction beginning to form downstream. The technique described in Omachi U.S. Pat. No. 5,454,374 has been used to measure the baseline pressure access site for early detection of such a pressure rise. Another method used by clinicians is to measure recirculation in the vessel during dialysis. As the flow is restricted at the point of access, the blood pumping rate indicated on the dialysis machine may exceed the flow rate of fresh blood coming into the vessel, so that some is recirculated from the venous access site to the arterial access site in the patient. This leads to inadequate dialysis since already cleansed blood is thus being reprocessed.

Various methods for measuring the degree of recirculation of this type are known. Another method described by Krivitsky determines blood flow in the access as a marker for stenosis. In this method blood set flow and recirculation is determined with arterial and venous flow reversed between the arterial and venous access sites, which are typically fistula needles which enter the vein. In the prior art, clinicians typically accomplish this by stopping the flow of blood, clamping off all the lines, disconnecting the set or sets from the fistula needles, and then reconnecting the arterial line to the venous fistula while connecting the venous line to the arterial fistula.

Also regarding catheters (which are typically connected to larger veins or even the vena cava) it is known that catheter blockage may be relieved by reversing flow.

By this invention, a flow set is provided for the communication of blood between a patient and a blood processing device in which the flow restriction at a patient access site can be easily monitored without any external disconnection of the connections needed for the normal flow of blood from a patient to a blood processing device such as a dialyzer, and then from the dialyzer back to the patient. Thus, a great improvement in the convenience of use of the tubular set of this invention is provided. Also, breaks in sterility are avoided, since there is no need to make external disconnections in order to test the patency of a patient access site. Also, the tubular set of this invention can be a combined arterial and venous set, while, most often in the prior art, a separate arterial set and a separate venous set are used. This provides convenience of use through the unification of the set.

Also, catheters which are implanted in the venous system of a patient for dialysis access or the like may develop a "fibrin sheath" on the outside of the catheter within the blood vessel, for example the jugular or subclavian veins or the vena cava. This fibrin sheath coats the outside of the catheter and can extend over the end thereof.

At the outflow port, this is generally not too serious a problem since the outflowing blood forces the fibrin sheath open easily. However, at the inflow port of the catheter, the sheath can act as a one way valve, collapsing with increasing negative pressure to seriously interfere with flow through the catheter.

Upon such an occurrence, by this invention, the blood flow through such a blood access catheter can be reversed for continuation of a desired medical procedure such as hemodialysis.

DESCRIPTION OF THE INVENTION

In this invention, a tubular set for the extracorporeal treatment of blood is provided. The set comprises a patient arterial line and a patient venous line, each line having a patient connector at one end thereof. Each said patient line connects at its other end to a reversing flow valve. The reversing flow valve also connects to respective first ends of a unit arterial line and a unit (or device) venous line. Each of the unit arterial and unit venous lines may carry a connector at ends opposed to their first ends for connection respectively to the arterial and venous ports of a blood processing device. Alternatively, the blood processing device may be directly and permanently connected to the unit arterial and venous lines.

The reversing flow valve has a first position that respectively connects the patient and unit arterial lines as one connected unit, and the patient and unit venous lines as another connected unit. The reversing flow valve also has a second position that connects the patient arterial line with the unit venous line, and the unit arterial line with a patient venous line. In this latter position, blood flow through the two patient lines can be reversed from the first position of the reversing flow valve, without reversing flow through the two unit lines and a connected blood processing device.

The flow of blood may be driven through the set by a blood pump, which preferably engages the unit arterial line or the unit venous line. Thus, the pump may continue to pump in a single direction of flow, and flow passes in single direction through the blood processing device (dialyzer) in unchanged direction, but the direction of flow through the patient arterial line and the patient venous line changes in a manner dependent upon the position of the reversing flow valve.

Thus, any of the known prior art techniques for measuring the degree of recirculation, for measuring flow, or for alleviating catheter blockage may be performed as the reversing flow valve occupies its second position, so that blood flow enters the patient through the arterial fistula needle and is drawn from the patient through the venous fistula needle. Then, the flow pattern can be quickly set back to normal by the simple adjustment of the reversing flow valve, with the blood flow proceeding first through the arterial set portions, through the blood processing device, and then through the venous set portions.

The reversing flow valve may comprise an outer sleeve member having four access ports connecting respectively to the patient and unit arterial lines, and the patient and unit venous lines. The valve also comprises a rotatable valve member which is sealingly positioned within the outer sleeve member. The reversing flow valve defines a pair of separate passageways that, in the first rotatable position of the valve, respectively connect the patient arterial line with the unit arterial line, and the patient venous line with the unit venous line. In the second rotational position of the valve, it respectively connects the patient arterial line with the unit venous line and the patient venous line with the unit arterial line. The separate passageways may be defined by the rotatable valve member, and may be straight, preferably comprising cylindrical holes extending transversely through the rotatable valve member.

The reversing flow valve of this invention can be free of dead legs (i.e. unused flow channel portions) and dead spaces as the valve is switched from position to position. Thus, few or no stagnant spaces are found where blood clotting can be enhanced. Also, the valve of this invention can be switched between its positions so quickly that dialysis machine pressure alarms are not set off even if the switching is performed while the blood pump is operating normally to pump blood through the set of this invention.

DESCRIPTION OF THE DRAWINGS

Referring to the drawings,

FIG. 3 is an elevational view, with portions broken away, of the reversing flow valve of this invention, shown to be occupying one of its flow controlling positions;

FIG. 4 is an elevational view, with portions broken away, of the valve of FIG. 3, shown in its other flow controlling position with the inner, rotatable valve member being rotated 90° from the configuration of FIG. 3;

FIG. 5 is a bottom plan view of the inner rotatable valve member of the valve of FIG. 3;

FIG. 6 is a longitudinal sectional view taken along line 6—6 of FIG. 4;

FIG. 7 is a longitudinal sectional view taken along line 7—7 of FIG. 3; and

FIG. 8 is an exploded, enlarged perspective view of the reversing flow valve of FIGS. 3–7.

DESCRIPTION OF THE SPECIFIC EMBODIMENTS

Figure 1:
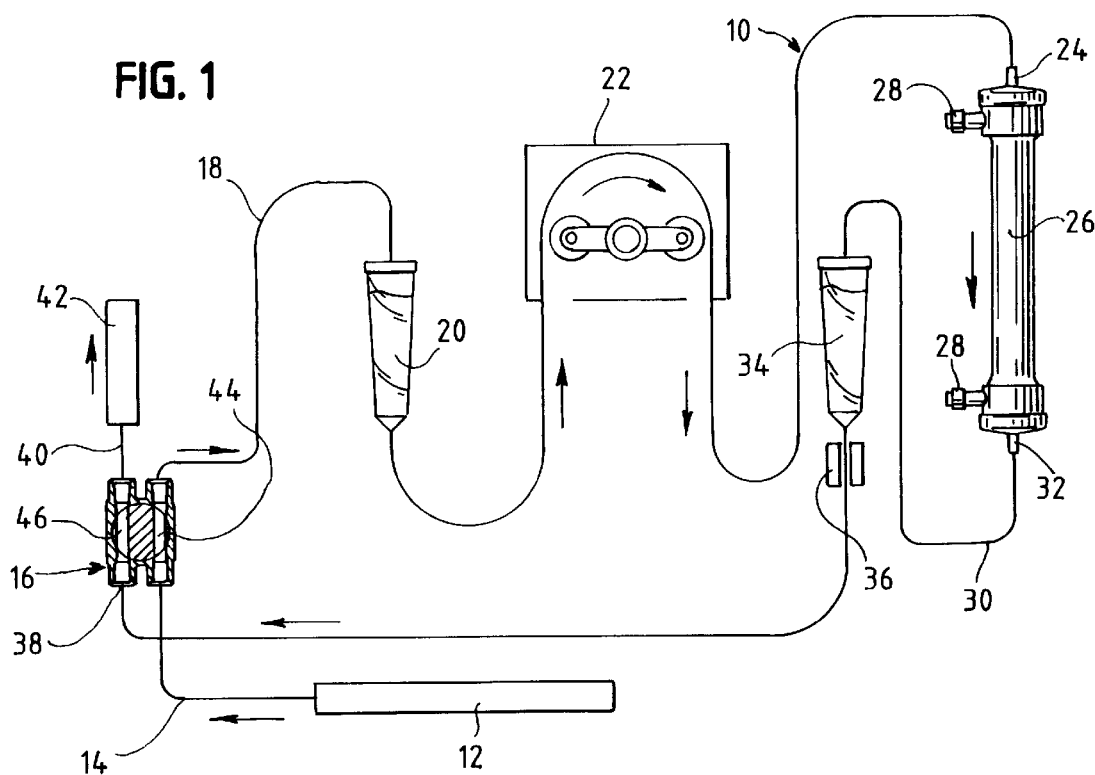
FIG. 1 is a schematic view of the tubular set of this invention for extracorporeal treatment of blood, shown to be connected to a dialyzer and to fistula needles for connection to a patient, and showing a first flow path through it.

Referring to the drawings, FIG. 1 shows a typical hemodialysis system 10 in which an arterial fistula needle 12 connected to a patient in conventional manner further connects to an arterial patient line 14 at one end thereof. The other end of arterial patient line 14 communicates with one port of reversing flow valve 16. In one position of valve 16, blood flows from patient arterial line 14, through the valve, into dialyzer arterial line 18, previously called the "unit arterial line". Blood flows through a bubble trap 20 in the dialyzer arterial line 18, and passes through a blood pump 22, typically in conventional manner, with dialyzer arterial line 18 communicating with the arterial end 24 of a conventional hollow fiber dialyzer 26. As is also conventional, ports 28 of dialyzer 26 provide a flow path for dialysis solution through the dialyzer.

A dialyzer venous line 30 (called the "unit venous line" previously) connects to the venous end 32 of dialyzer 26. Dialyzer venous line 30 passes through another bubble trap 34, through a bubble detector 36, and connects at its other end 38 to reversing flow valve 16. Blood from line 30 passes through reversing flow valve 16 in the position shown in FIG. 1 to flow into patient venous line 40 which, in turn, connects to a venous fistula needle 42 for return of blood to the patient. The arterial and venous fistula needles shown herein may be replaced with other devices which perform the same function of withdrawing from and returning blood to the patient in some manner. Both needles 12 and 42 may be placed into an arteriovenous fistula, for example on the arm of a patient, for blood access.

FIG. 1 shows the normal flow configuration for blood, with the flow being indicated by the various arrows, where the blood passes through the arterial lines 14, 18 to the dialyzer 26, and then passes through the venous lines 30, 40 back to the patient. It can be seen that reversing flow valve 16 has a pair of separate, parallel flow channels 44, 46. Flow channel 44 is for arterial line blood flow and flow channel 46 is for venous line blood flow.

Then, when there is a need to determine the patency of a patient's vascular access site, reversing flow valve 16 may simply be turned to a second flow condition in which the flow through the respective patient lines 14, 40 is reversed as shown by the arrows, while the flow through the respective dialyzer (unit) lines 18, 30, and the flow through dialyzer 26, remains unchanged. Thus, pump 22 also operates in unchanged manner during this change in procedure, which is typically a brief change. The specific methods of testing are conventional and known, but may require this reversal of flow in patient lines 14 and 40.

Figure 2:
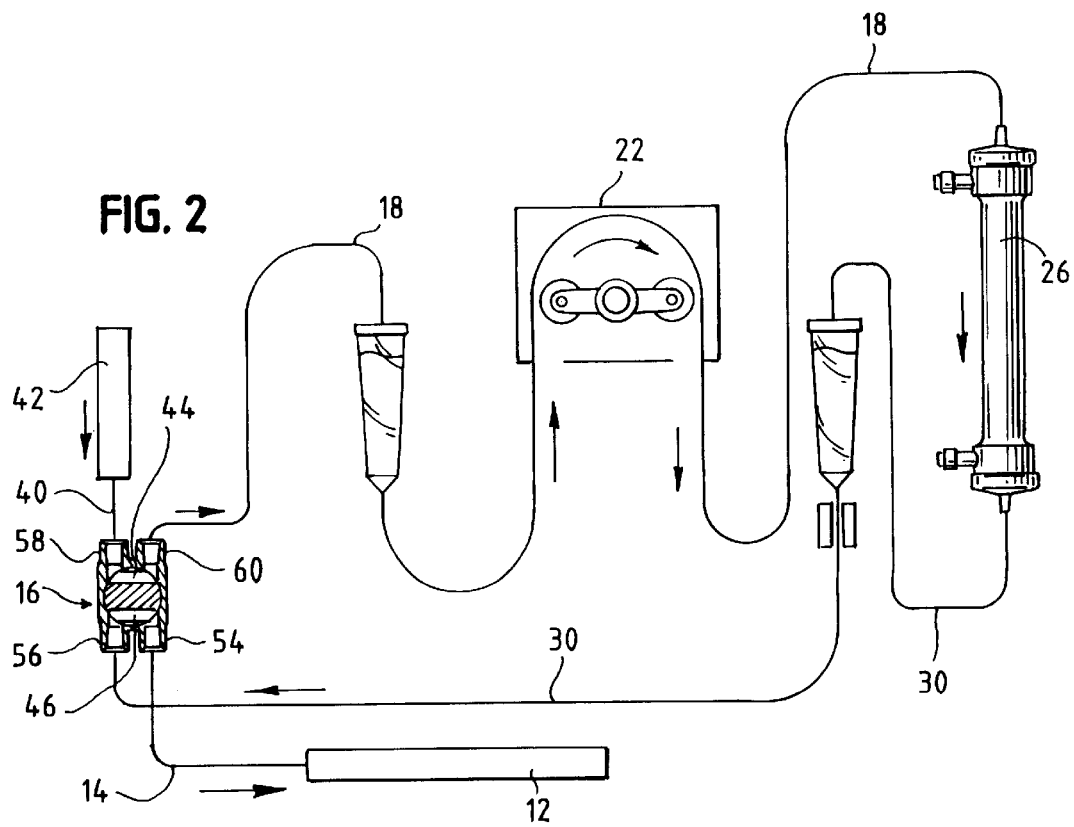
FIG. 2 is a schematic view of the set of FIG. 1, showing an alternate flow pattern provided by the reversing flow valve of this invention.

Thus, in the second valve position shown in FIG. 2, patient arterial line 14 connects with dialyzer (unit) venous line 30, while patient venous line 40 connects with dialyzer arterial line 18. Thus, as roller pump 22 continues operation, blood is drawn through venous fistula needle 42 into the system in a direction of flow opposite to that of FIG. 1, while blood is expelled back to the patient through arterial fistula needle 12 in a flow direction that is opposite to that of FIG. 1. This makes possible desired testing for patient access site patency. Also, blood can be once again obtained from an implanted catheter even when the flow in the opposite direction has been inhibited because of a fibrin sheath.

While the term "dialyzer" is used, it is intended that the invention herein may be used in any extracorporeal blood treatment process, and is not limited to use in the field of dialysis.

As shown by FIGS. 3–7, reversing flow valve 16 comprises an outer sleeve member 50. Outer sleeve member 50, as shown in FIG. 8, comprises a sleeve portion 52, which is open at both ends in this particular embodiment, but may have a closed end if desired. Four access ports 54, 56, 58, 60 connect with and communicate through the wall of outer sleeve 52. These access ports then communicate with the respective lines 14, 18, 30, 40 as shown particularly in FIGS. 1 and 2.

Valve 16 also comprises a rotatable valve member 62 (FIG. 8), having a rotatable barrel 64 that fits within sleeve 50, plus an integral handle 66 connected to barrel 64. Also, various seal grooves 68 are provided on barrel 64, which grooves may contain conventional O-rings 69 for sealing. Groove 71 may receive an end of sleeve member 50.

Barrel 64 may comprise an open tube, closed by a partition 70. Barrel 64 also defines a pair of spaced, parallel cylindrical bores 44, 46 that are defined within the structure of barrel 64 as particularly shown in FIG. 7. These bores 44, 46 are specifically positioned to connect between the respective inner ends 76 (FIG. 8) of ports 54–60, to provide two different connection positions for selective connection of the respective lines 14, 18, 30, and 40, for purposes as previously described. These connection positions can be seen by comparing FIG. 1 and FIG. 2, and the respective positions of bores 44, 46.

In FIG. 3, bore 46 is extending parallel to the plane of the paper, with the two ends being shown in full lines. In FIG. 4, bores 44, 46 are perpendicular to the plane of the paper. An FIG. 8, diametrically disposed stops 73 and rib 72 may limit the rotation of valve member 62 in sleeve member 50 to a desired range, specifically 90°

Thus, a set for extracorporeal blood processing is provided in which the flow through the patient fistula connectors can be reversed as desired, for the benefits described above, and without the need for disconnection of set components from each other.

The above has been offered for illustrative purposes only, and is not intended to limit the scope of the invention of this application, which is as defined in the claims below.

What is claimed is:

1. A tubular set for the extracorporeal treatment of blood, said set comprising a device arterial line, a device venous line, a patient arterial line, a patient venous line, and a reversing flow valve, each said patient line having a patient connector at one end thereof, each said patient line being connected at its other end to said reversing flow valve, said valve also being connected to respective first ends of said device arterial line and device venous line, each of said device lines carrying a connector at ends opposed to the first ends for connection respectively to arterial and venous ports of a blood processing device, said reversing flow valve being movable between a first position that respectively connects the patient and device arterial lines and the patient and device venous lines and a second position that respectively connects the patient arterial line with the device venous line, and the device arterial line with the patient venous line, whereby blood flow trough the two patient lines can be reversed without reversing flow through the two device lines and a connected blood processing device, when the set is connected to a blood pump.

2. The set of claim 1 in which said reversing flow valve comprises an outer sleeve member having four access ports connected respectively to the patient and device arterial lines and the patient and device venous lines, said valve further comprising a rotatable valve member sealingly positioned within said outer sleeve member, said flow valve defining a pair of separate passageways which, in a first rotatable position of said valve, respectively connect said patient arterial line with the device arterial line, and the patient venous line with the device venous line, and in a second rotatable position of said valve member respectively connect said patient arterial line with the device venous line and the patient venous line with the device arterial line.

3. The tubular set of claim 2 in which said separate passageways are defined by said rotatable valve member, and are straight.

4. The tubular set of claim 3 in which said reversing flow valve is free of unused flow channel portions in both said first and said second positions to reduce stagnant spaces where blood clotting can be enhanced.

5. The tubular set of claim 4 in which said reversing flow valve carries a manually graspable handle to move said valve between the first and second positions.

6. The tubular set of claim 3 in which said flow valve is free of dead legs in both positions.

7. The tubular set of claim 1 in which said reversing flow valve is free of unused flow channel portions in both said first and said second positions to reduce stagnant spaces where blood clotting can be enhanced.

8. The tubular set of claim 7 in which said reversing flow valve carries a manually graspable handle to move said valve between the first and second positions.

9. The tubular set of claim 1 in which catheter comprises at least part of said patient arterial line and patient venous line.

10. The method of performing an extracorporeal treatment of blood which comprises: (1) drawing blood from a patient through a patient arterial line and passing said blood from the patient arterial line to a device arterial line; passing blood from the device arterial line to a blood treatment device; passing blood from the blood treatment device to a device venous line; passing blood from the device venous line to a patient venous line and from there back to the patient, said process further including the step of (2) manually switching the connections of said lines without external disconnection and reconnection and, thereafter, (3) passing blood from the patient through the patient venous line to the device arterial line; passing blood from the device arterial line through the connected blood processing unit to the device venous line; passing blood from the device venous line to the patient arterial line, and returning blood from the patient arterial line to the patient.

11. The method of claimed 10 in which the four respective lines are each connected to a reversing flow valve having a manually movable valve control for manually switching the connections, and said movable valve control is moved after performing step (1) and before performing step (3).

12. The method of claim 11 in which the method of manually switching the connections of said lines without external disconnection is performed with a system that is free of unused flow channel portions both before and after said switching to avoid stagnant spaces where blood clotting is enhanced.

13. The method of claim 12 in which said movable valve control is manually moved while continuing flow of blood through said lines.

14. The method of claim 11 in which said extracorporeal treatment of blood comprises a hemodialysis process.

15. The method of claim 11 in which said movable valve control is moved while continuing flow of blood through said lines.

16. The method of claim 10 in which catheter comprises at least part of said patient arterial line and patient venous line.

17. A tubular set for the extracorporeal treatment of blood, said set comprising a device arterial line, a device venous line, a patient arterial line, a patient venous line, and a reversing flow valve, each of said patient lines having a patient connector at one end thereof, each said patient line being connected at its other end to said reversing flow valve, said valve also being connected to respective first ends of said device arterial line and device venous line, each of said device lines carrying a connector at ends opposed to the first ends for connection respectively to arterial and venous ports of a blood processing device, said reversing flow valve comprising an outer sleeve member having four access ports connected respectively to the patient and device arterial lines and the patient and device venous lines, said valve further comprising a rotatable valve member sealingly positioned within said outer sleeve member, said flow valve defining a pair of separate passageways which, in a first rotatable position of said valve member, respectively connect said patient arterial line with the device arterial line and the patient venous line with the device venous line, and in a second rotatable position of said valve member respectively connect said patient arterial line with the device venous line and the patient venous line with the device arterial line, said flow valve being substantially free of unused flow channel portions to reduce stagnant spaces in said flow valve where blood clotting can be enhanced, said flow valve also carrying a manually graspable handle connected to said rotatable valve member to facilitate manual rotation of said valve member, whereby blood flow through the patient lines can be reversed without reversing flow through the device lines and a connected blood processing device, when the set is connected to blood pump.

18. The set of claim 17 in which said unit arterial line carries a length of roller pump tubing.

19. The blood processing system of claim 18 in which said separate passageways are defined by said rotatable valve member, and are straight.

20. The tubular set of claim 17 in which catheter comprises at least part of said patient arterial line and patient venous line.

* * * * *